(12) United States Patent
Nguyen et al.

(10) Patent No.: US 12,385,751 B2
(45) Date of Patent: Aug. 12, 2025

(54) APPARATUSES AND METHODS FOR PROVIDING GUIDANCE WHILE PERFORMING TASKS

(71) Applicant: Micron Technology, Inc., Boise, ID (US)

(72) Inventors: Linh H. Nguyen, Boise, ID (US); Barbara J. Bailey, Kuna, ID (US); Caixia Yang, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 383 days.

(21) Appl. No.: 17/748,149

(22) Filed: May 19, 2022

(65) Prior Publication Data

US 2023/0375353 A1 Nov. 23, 2023

(51) Int. Cl.
*G01C 21/34* (2006.01)
*A61B 34/00* (2016.01)
*G01C 21/36* (2006.01)

(52) U.S. Cl.
CPC .......... *G01C 21/3484* (2013.01); *A61B 34/25* (2016.02); *G01C 21/3629* (2013.01); *A61B 2034/252* (2016.02)

(58) Field of Classification Search
CPC ............ G01C 21/3484; G01C 21/3629; G01C 21/3617; G01C 21/3415; A61B 34/25; A61B 2034/252
See application file for complete search history.

(56) References Cited

U.S. PATENT DOCUMENTS

| | | | |
|---|---|---|---|
| 2017/0108342 A1* | 4/2017 | Foreman | G01C 21/3691 |
| 2018/0005523 A1* | 1/2018 | Cahan | G08G 1/096775 |
| 2018/0317798 A1* | 11/2018 | Amitai | G16Z 99/00 |
| 2018/0348759 A1* | 12/2018 | Freeman | A61N 1/3904 |
| 2020/0143940 A1* | 5/2020 | Yasui | G16H 40/20 |
| 2020/0182636 A1* | 6/2020 | Ningthoujam | G08G 1/096725 |
| 2021/0088346 A1* | 3/2021 | Lautenschlaeger | G16H 50/20 |
| 2021/0158233 A1* | 5/2021 | Lakshminarayanan | H04W 4/024 |
| 2021/0407273 A1 | 12/2021 | Jafri et al. | |
| 2021/0407665 A1* | 12/2021 | Simha | G16H 10/60 |
| 2022/0003562 A1 | 1/2022 | Mack et al. | |
| 2022/0044505 A1 | 2/2022 | Eickhoff et al. | |
| 2022/0150794 A1 | 5/2022 | Sparks et al. | |
| 2022/0157165 A1 | 5/2022 | Dantrey et al. | |
| 2022/0315061 A1* | 10/2022 | Ishikawa | B60Q 1/52 |

(Continued)

*Primary Examiner* — Anne Marie Antonucci
*Assistant Examiner* — Patrick Daniel Mohl
(74) *Attorney, Agent, or Firm* — Brooks, Cameron & Huebsch, PLLC

(57) ABSTRACT

Apparatuses, media, and methods associated with providing guidance while performing tasks are described. Guidance can be provided in the form of directions for reaching a destination. For example, the guidance can include determining a destination and/or providing directions to reach the destination in the least amount of time. The guidance can include directions in the form of audible turn by turn instructions, a route shown on a map, and/or indications by streetlights or street signs (e.g., the route to the destination is indicated by flashing streetlights or words shown on street signs), among other types of guidance. Guidance can be provided in the form of instructions for performing a task. For example, the guidance can include instructions for treating a medical condition of an individual in an ambulance.

17 Claims, 4 Drawing Sheets

(56) References Cited

U.S. PATENT DOCUMENTS

2023/0078911 A1\* 3/2023 Resnik ............... G01C 21/3461
                                                          701/533
2023/0162595 A1\* 5/2023 Seder ............... G08G 1/096716
                                                          701/428

\* cited by examiner

APPARATUSES AND METHODS FOR PROVIDING GUIDANCE WHILE PERFORMING TASKS

TECHNICAL FIELD

The present disclosure relates generally to apparatuses, media, and methods associated with providing guidance while performing tasks.

BACKGROUND

A computing device is a mechanical or electrical device that transmits or modifies energy to perform or assist in the performance of human tasks. Examples include thin clients, personal computers, printing devices, laptops, mobile devices (e.g., e-readers, tablets, smartphones, etc.), internet-of-things (IoT) enabled devices, and gaming consoles, among others. An IoT enabled device can refer to a device embedded with electronics, software, sensors, actuators, and/or network connectivity which enable such devices to connect to a network and/or exchange data. Examples of IoT enabled devices include mobile phones, smartphones, tablets, phablets, computing devices, implantable devices, vehicles, home appliances, smart home devices, monitoring devices, wearable devices, devices enabling intelligent shopping systems, among other cyber-physical systems.

A computing device can be used to transmit information to users via a display to view images and/or text, speakers to emit sound, and/or a sensor to collect data. A computing device can receive inputs from sensors on or coupled to the computing device. The computing device can be coupled to a number of other computing devices and can be configured to communicate (e.g., send and/or receive data) with the other computing devices and/or to a user of the computing device.

DETAILED DESCRIPTION

Figure 1:
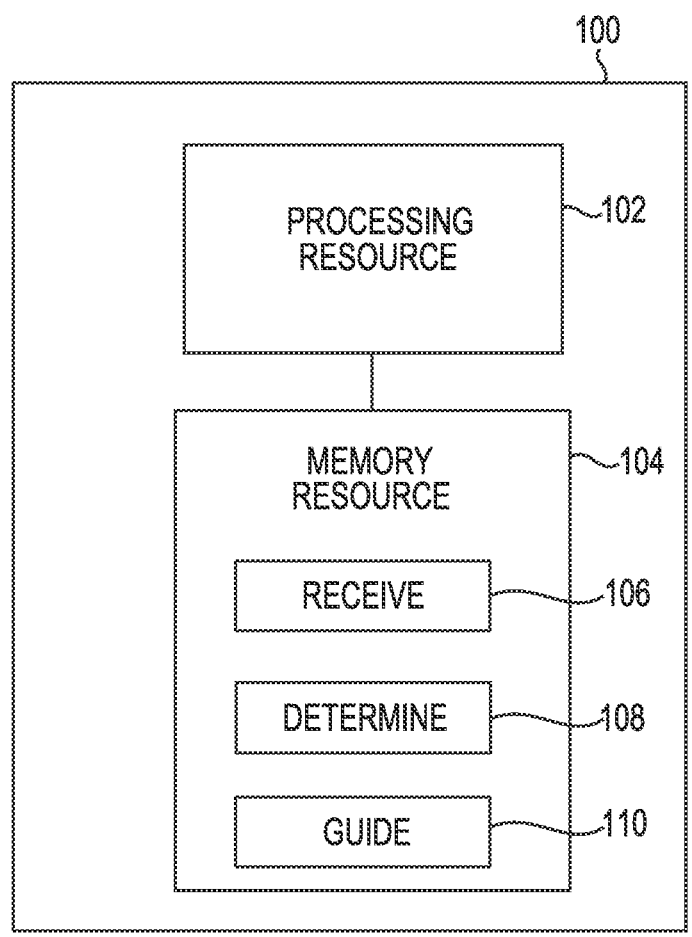
FIG. 1 is a diagram representing an apparatus including a processing resource and a memory resource in accordance with a number of embodiments of the present disclosure.

Apparatuses, media, and methods associated with providing guidance while performing tasks are described. Guidance can be provided in the form of directions for reaching a destination. For example, the guidance can include determining a destination and/or providing directions to reach the destination in the least amount of time. The guidance can include directions in the form of audible turn by turn instructions, a route shown on a map, and/or indications by lights long a roadway, streetlights or street signs (e.g., the route to the destination is indicated by flashing lights, streetlights, or words shown on street signs), among other types of guidance. Guidance can be provided in the form of instructions for performing a task. For example, the guidance can include instructions for treating a medical condition of an individual in an ambulance. The guidance can be based on a condition of the individual, the amount of time that a vehicle, such as an ambulance, will take to get to the destination, and/or the capabilities of the ambulance and/or first responders to provide treatment.

Examples of the present disclosure allow for providing guidance while performing a task. The guidance can be determined using artificial intelligence (AI) and/or a machine learning model. The guidance can be helpful in certain situations where a user may be multi-tasking and/or the conditions for performing the task are changing and/or unknown to a user. For instance, guidance can be provided to first responders in an ambulance. The first responders can be preoccupied with treating an individual experiencing a medical emergency and embodiments of the present disclosure can determine a medical facility to bring the individual (e.g., a destination) and/or determine a route that takes the least amount of time to reach the medical facility. Guidance can also be provided to first responders in the ambulance that includes instructions on how to provide medical treatment to the individual. The machine learning model can use information regarding the condition of the individual, the capabilities of the ambulance and/or first responders, and the current location of the ambulance to determine a medical treatment. Instructions for performing the medical treatment can be provided to the first responders.

Examples of the present disclosure can include an apparatus comprising a processing resource and a memory resource in communication with the processing resource having instructions executable to receive, at the processing resource, the memory resource, or both, and from a first source, status information regarding a current state of a first individual, determine a destination for the first individual based on the current state of the first individual, and provide guidance to reach the destination based on the current state of the first individual or the determined destination for the first individual.

In the following detailed description of the present disclosure, reference is made to the accompanying drawings that form a part hereof, and in which is shown by way of illustration how one or more embodiments of the disclosure can be practiced. These embodiments are described in sufficient detail to enable those of ordinary skill in the art to practice the embodiments of this disclosure, and it is to be understood that other embodiments can be utilized and that process, electrical, and structural changes can be made without departing from the scope of the present disclosure.

It is also to be understood that the terminology used herein is for the purpose of describing particular embodiments only and is not intended to be limiting. As used herein, the singular forms "a," "an," and "the" can include both singular and plural referents, unless the context clearly dictates otherwise. In addition, "a number of," "at least one," and "one or more" (e.g., a number of memory devices) can refer to one or more memory devices, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to." The terms "coupled," and "coupling" mean to be directly or indirectly connected physically or for access to and movement (transmission) of commands and/or data, as appropriate to the context.

The figures herein follow a numbering convention in which the first digit or digits correspond to the figure number and the remaining digits identify an element or component in the figure. Similar elements or components between different figures can be identified by the use of similar digits. For example, 100 can reference element "00" in FIG. 1, and a similar element can be referenced as 200 in FIG. 2. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1 is a diagram representing an apparatus 100 including a processing resource 102 and a memory resource 104 in accordance with a number of embodiments of the present disclosure. The memory resource 104 can be in communication with the processing resource 102, and the memory resource 104 may have instructions written thereon. The apparatus 100, in some examples, can include a controller, such as a microcontroller. The processing resource 102, the memory resource 104, or both, may be part of the controller or separate from the controller.

In some examples, the apparatus 100 can utilize artificial intelligence (AI) and associated machine learning models to determine and update instructions associated with performance of the apparatus 100. AI, as used herein, includes a controller, computing device, or other system to perform a task that normally requires human intelligence. For instance, the controller, processing resource 102, memory resource 104 or any combination thereof can perform a task (e.g., providing guidance while performing a task) that normally requires human intelligence. In some examples, the apparatus 100 can act as a local source of processing and storage while sending data to cloud storage or to sources in communication with the apparatus 100.

The apparatus 100, in some examples, may be in communication with a sensor or sensors (not illustrated in FIG. 1) associated with the sources (e.g., location and/or status information). For example, the memory resource 104 of the apparatus 100 may be in communication with the sensor or sensors. Example sensors may include cameras or other image sensors, temperature sensors, health monitoring sensors (e.g., heart rate, blood sugar, etc., among other health monitoring sensors), location sensors (e.g., GPS or other location monitor), depth sensors, particle/smoke sensors, or battery sensors, among others.

At 106, the processing resource 102 can execute instructions to receive, at the processing resource 102, the memory resource 104, or both, and from a first source, location and/or status information. For instance, the location information can be a location of an individual and the status information can be a medical condition of the individual. The status information can be received from any type of source, such as a number of sensors and/or from information relayed to and/or determined by first responders. The location and/or status information can be periodically updated.

At 108, the processing resource 102 can execute instructions to determine a destination based on the location and/or status information, a route to reach the destination in the least amount of time, and/or instructions to perform a task (e.g., provide instruction to perform a medical treatment to an individual).

Such examples can use a machine learning model, for instance to determine the route to reach the destination in the least amount of time, determine the destination based upon the location and/or status information, determine the destination based upon the capabilities of the destination. For example, a medical facility with a trauma center can be determined to be the destination in response to a medical emergency with life-threatening injuries. Instructions to perform a task can be determined based on the status and/or location information. The status information can include a medical condition of an individual. The status information can be used to determine the type of medical procedures that can help the individual while enroute to the destination. The instructions to perform a task can be communicated via audio and/or visually via a computing device.

At 110, the processing resource 102 can execute instructions to provide guidance to reach the destination and/or guidance to perform a task. For instance, guidance to reach the destination can include a route shown on a map and/or turn by turn instructions relayed via the audio system of a vehicle. The guidance to reach the destination can also include indications (such as flash streetlights) that show the route to the destination. Guidance can also include instructions to perform a task. The instructions can be instructions to perform a medical procedure on an individual. The instructions can be based upon the capabilities of the emergency vehicle (e.g., the equipment in the emergency vehicle), the capabilities of the first responders providing the treatment, the capabilities of the destination medical facility, the distance from the destination medical facility, and/or the medical condition and/or history of the individual that is being treating, among other factors.

Figure 2:
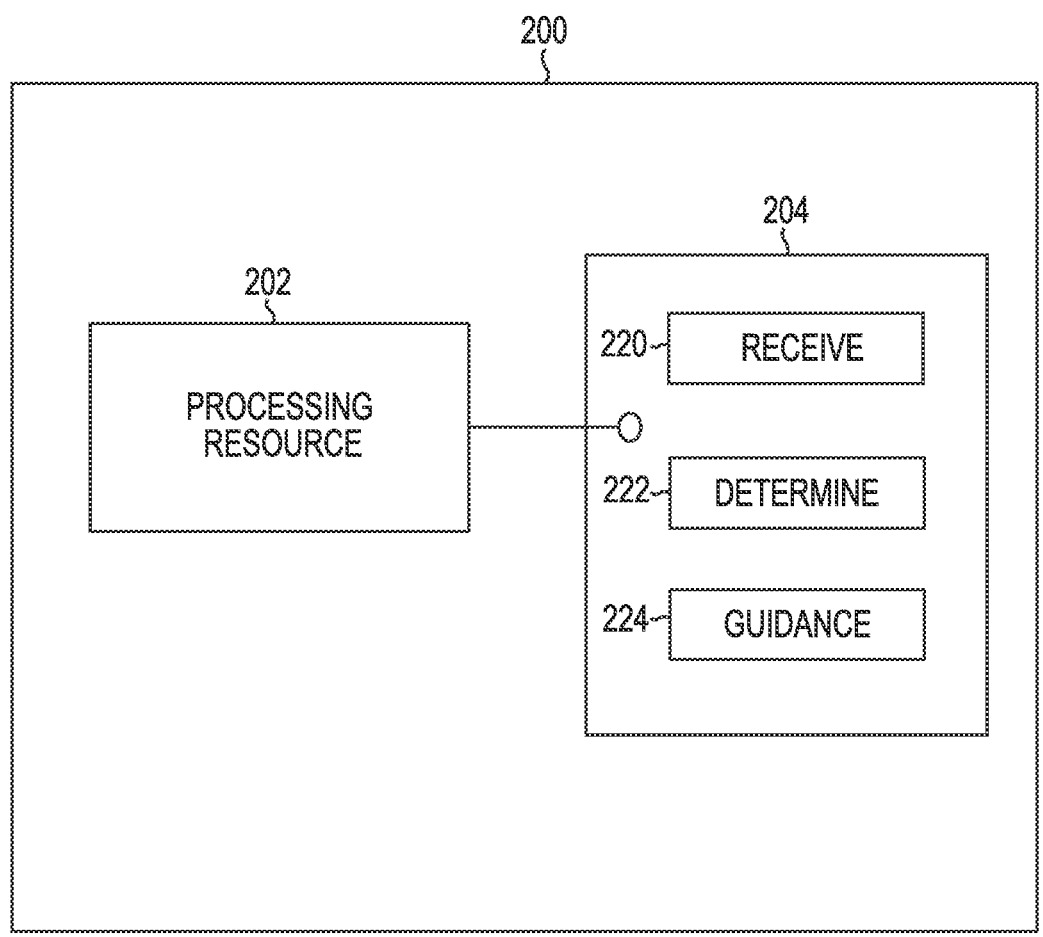
FIG. 2 is a functional diagram representing a processing resource in communication with a memory resource having instructions written thereon in accordance with a number of embodiments of the present disclosure.

FIG. 2 is a functional diagram representing a processing resource 202 in communication with a memory resource 204 having instructions 220, 222, and 224 written thereon in accordance with a number of embodiments of the present disclosure. In some examples, the processing resource 202 and the memory resource 204 comprise an apparatus 200 such as the apparatus 100 illustrated in FIG. 1. In some examples, the processing resource 202 and the memory resource 204 comprise a microcontroller.

The apparatus 200 illustrated in FIG. 2 can be a server or a computing device (among others) and can include the processing resource 202. The apparatus 200 can further include the memory resource 204 (e.g., a non-transitory MRM), on which may be stored instructions, such as instructions 220, 222, and 224. Although the following descriptions refer to a processing resource and a memory resource, the descriptions may also apply to a system with multiple processing resources and multiple memory resources. In such examples, the instructions may be distributed (e.g., stored) across multiple memory resources and the instructions may be distributed (e.g., executed by) across multiple processing resources.

The memory resource 204 may be electronic, magnetic, optical, or other physical storage device that stores executable instructions. Thus, the memory resource 204 may be, for example, non-volatile or volatile memory. For example, non-volatile memory can provide persistent data by retaining written data when not powered, and non-volatile memory types can include NAND flash memory, NOR flash memory, read only memory (ROM), Electrically Erasable Programmable ROM (EEPROM), Erasable Programmable ROM (EPROM), and Storage Class Memory (SCM) that can include resistance variable memory, such as phase change random access memory (PCRAM), three-dimensional cross-point memory, resistive random access memory (RRAM), ferroelectric random access memory (FeRAM), magnetoresistive random access memory (MRAM), and programmable conductive memory, among other types of memory. Volatile memory can require power to maintain its data and can include random-access memory (RAM), dynamic random-access memory (DRAM), and static random-access memory (SRAM), among others.

In some examples, the memory resource 204 is a non-transitory MRM comprising Random Access Memory (RAM), an Electrically-Erasable Programmable ROM (EEPROM), a storage drive, an optical disc, and the like. The memory resource 204 may be disposed within a controller (e.g., microcontroller) and/or computing device. In this example, the executable instructions 220, 222, and 224 can be "installed" on the device. Additionally, and/or alternatively, the memory resource 204 can be a portable, external or remote storage medium, for example, which allows the system to download the instructions 220, 222, and 224 from the portable/external/remote storage medium. In this situation, the executable instructions may be part of an "installation package". As described herein, the memory resource 204 can be encoded with executable instructions associated with updating a map using images.

The instructions 220, when executed by a processing resource such as the processing resource 202, can include instructions to receive, at the processing resource 202, the memory resource 204, or both, location and/or status information. The location information can be an initial location of an individual (e.g., GPS information and/or address information for an individual who has requested assistance). The status information can include a medical condition of an individual and/or a desired outcome or destination for an individual. The status information can also include the capabilities of the emergency vehicle (e.g., the equipment in the emergency vehicle), the capabilities of the first responders providing the treatment, the capabilities of the destination medical facility, the distance from the destination medical facility, and/or the medical condition and/or history of the individual that is being treating, among other status information.

The instructions 222, when executed by a processing resource such as the processing resource 202, can include instructions to determine, at the processing resource 202, the memory resource 204, or both, a destination for the individual and/or instructions for performing a task. The instructions can be communicated via audible words delivered via a speaker, written words delivered via a graphical interface, and/or visual depictions (e.g., diagrams or maps) delivered via a graphical interface, for example.

The instructions 224, when executed by a processing resource such as the processing resource 202, can include instructions to provide guidance to reach a destination and/or provide guidance including instructions for performing a task. The guidance to reach a destination can include a route that allows for the emergency vehicle to reach the destination in the shortest amount of time. The guidance to reach a destination can include a route to a medical facility that has the capabilities to treat the individual that is in need of medical treatment. The guidance can include audible turn by turn instructions, a route shown on a map, and/or indications by lights long a roadway, streetlights or street signs (e.g., the route to the destination is indicated by flashing lights, streetlights, or words shown on street signs), among other types of guidance.

Figure 3:
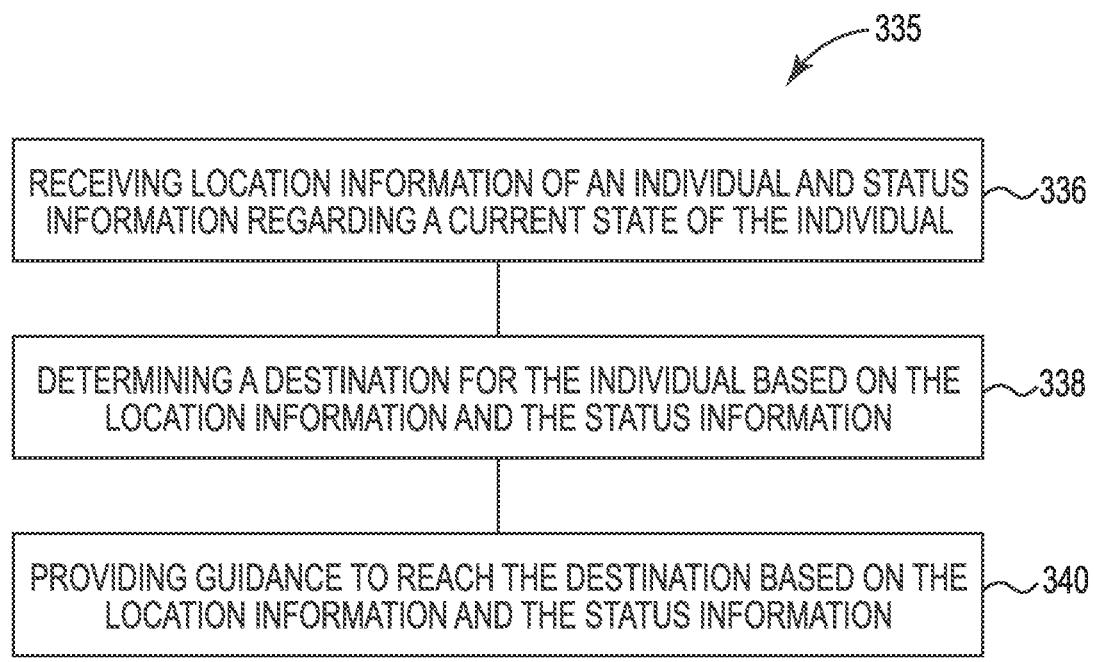
FIG. 3 is a flow diagram representing an example method associated with providing guidance while performing tasks in accordance with a number of embodiments of the present disclosure.

FIG. 3 is a flow diagram representing an example method 335 with providing guidance while performing tasks associated with a number of embodiments of the present disclosure. The method 335 may be performed using apparatus 100 or apparatus 200, as provided in FIG. 1 and FIG. 2, respectively.

At 336, the method 335 can include receiving, at a processing resource, a memory resource, or both, location information of an individual and status information regarding a current state of the individual. The location information can be acquired from a mobile device of the individual or of an individual called for assistance. The location information can be associated with a driver or passenger in a vehicle that is arriving to or leaving an event or traveling to a destination where the route is congested, an individual in an ambulance, or an individual seeking assistance.

The method 335, at 338, can include determining, at the processing resource, a destination for the individual based on the location information and the status information. The destination can be determined based on the status information, such as a medical condition of the individual, and the ability of a facility to treat the individual. For instance, if an individual has an accident where emergency treatment is needed, a medical facility with a trauma center can be determined to be the destination. Also, a preferred or previously used medical facility of the individual can be determined to be the destination.

In the situation where an individual is arriving or leaving an event, a desired destination, such a parking lot or restaurant, can be determined to be the destination.

At 340, the method 335 can include providing guidance to reach the destination based on the location information and the status information. The guidance can include directions to the destination in order to arrive at the destination in the least amount of time. The directions can be shown on a map, audible turn by turn directions of the route, or indicated by lights along the route. The lights along the route can be used to identify the route for a vehicle to take to the destination. The lights along the route can also indicate to other vehicles along the route that an emergency vehicle is approaching. For example, flashing red light along the route (e.g., on a streetlight post) can indicate that an emergency vehicle is approaching and other vehicles should pull over to the shoulder. Also, the lights can flash with increasing frequency to indicate that the emergency vehicle is approaching that portion of the roadway. The frequency of the flashing light can be proportional to the amount of time that the emergency vehicle will take to reach that portion of the roadway. For example, the lights can flash every 3 seconds if the emergency vehicle is 3 minutes away, the lights can flash every 2 seconds if the emergency vehicle is 2 minutes away, and lights can flash every 1 second if the emergency vehicle is 1 minute away.

Figure 4:
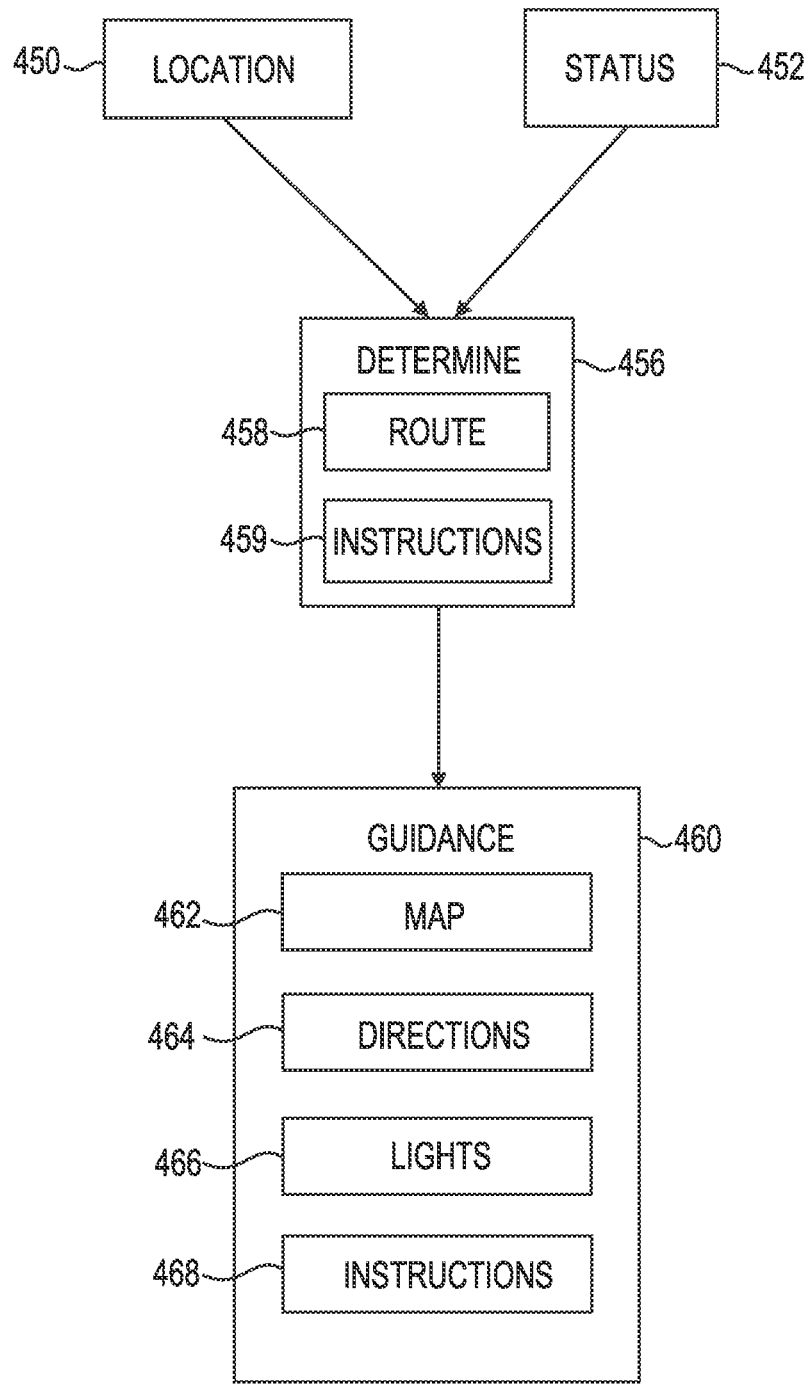
FIG. 4 is another flow diagram representing an example method associated with providing guidance while performing tasks in accordance with a number of embodiments of the present disclosure.

FIG. 4 is another flow diagram representing an example method associated with providing guidance while performing tasks in accordance with a number of embodiments of the present disclosure.

At 450, location information is provided. The location information can be based on sensor data (e.g., from a GPS sensor) and/or from information (e.g., address information) communication by an individual.

At 452, status information is provided. The status information can include a medical condition of an individual and/or a desired outcome or destination for an individual, among other types of status information. Status information can include the capabilities of the emergency vehicle (e.g., the equipment in the emergency vehicle), the capabilities of the first responders providing the treatment, the capabilities of the destination medical facility, the distance from the destination medical facility, and/or the medical condition and/or history of the individual that is being treating, among other factors.

At 456, an AI or machine learning model can use the location information and/or status information, among other types of data, to determine a route 458 to take to a destination and/or instructions 459 for performing a task. The route can be based upon the amount of time to reach the destination and/or the capabilities of the destination to provide services (e.g., medical treatment) to an individual.

At 460, guidance for performing a task can be provided. The guidance can include a map 462 indication a route to a destination. The guidance can include the route being highlighted on a map and can also include distance and turn based instructions that describe the route.

The guidance can include directions 464 along a route to reach a destination. The directions can include the names of roads, distance traveled on the roads, and turn by turn instructions so that the destination can be reached in the least amount of time.

The guidance can include instructions to cause lights to flash 466 along a route to a destination. The flashing lights can indicate the route to the destination. Also, the flashing lights can indicate that a vehicle, such as an emergency vehicle, are traveling on the route. The flashing lights can indicate to other vehicles on the route that they should pull the shoulder allowing the emergency vehicle to reach the destination quickly and safely.

The guidance can include instructions 468 for performing a task. The instructions for performing the task can include instructions for treatment procedures on an individual that is seeking help. The treatment procedures can be based upon the condition of the individual, the capabilities of the equipment in the ambulance, the capabilities of the destination medical facility, and/or the amount of time to reach the medical facility.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An apparatus, comprising:
a processing resource; and
a memory resource in communication with the processing resource having instructions executable to:
receive, at the processing resource, the memory resource, or both, and from a first source, status information regarding a current state of a first individual, and, from a second source, status information regarding a capability of an emergency vehicle that is responding to the first individual;
perform operations in a machine learning model to determine and output a destination for the emergency vehicle that is responding to the first individual, wherein the machine learning model determines the destination for the emergency vehicle based on the current state of the first individual, the capability of the emergency vehicle that is responding to the first individual to treat the first individual, a capability of the destination to treat the first individual, and a distance from a current location to the destination;
provide guidance to reach the destination based on the current state of the first individual or the determined destination for the first individual, wherein the output of the machine learning model provides the guidance through audio and visual indicators to a second individual in the emergency vehicle and wherein a light on a streetlight post flashes with a particular frequently along a route to the destination for the emergency vehicle to indicate the route to a driver of the emergency vehicle and to notify other vehicles of a location of the emergency vehicle on the route; and perform operations in a machine learning model to determine and output a medical treatment procedure to provide to the first individual by a third individual in the emergency vehicle that is responding to the first individual based on the current state of the first individual, the capability of the emergency vehicle that is responding to the first individual to treat the first individual, and the capability of the destination to treat the first individual, and the distance from a current location to the destination; and provide audio and/or visual guidance to third individual in the emergency vehicle for performing the medical treatment procedure on the first individual, wherein the output of the machine learning model provides the guidance through audio and visual indicators to the third individual in the emergency vehicle.

2. The apparatus of claim 1, wherein the current state of the first individual includes a location of the individual.

3. The apparatus of claim 1, wherein the current state of the first individual includes a medical condition of the individual.

4. The apparatus of claim 1, wherein the determined destination is a medical facility and the guidance includes a route to drive to the medical facility.

5. The apparatus of claim 1, further comprising instructions executable to indicate the route to other vehicles.

6. The apparatus of claim 1, further comprising instructions executable to provide instructions on how to perform the medical treatment procedure.

7. A non-transitory machine-readable medium comprising a processing resource in communication with a memory resource having instructions executable to:
receive, at the processing resource, the memory resource, or both, information regarding an initial location;

perform operations in a machine learning model, at the processing resource, the memory resource, or both, to determine and output a route to the initial location;
provide guidance to follow the route to the initial location;
receive, at the processing resource, the memory resource, or both, status information regarding a current state of an individual at the initial location and status information regarding a capability of an emergency vehicle that is responding to the individual;
perform operations in a machine learning model, at the processing resource, the memory resource, or both, to determine and output a destination for the individual, wherein the machine learning model determines the destination for the emergency vehicle based on the current state of the first individual, the capability of the emergency vehicle that is responding to the first individual to treat the first individual, a capability of the destination to treat the first individual, and a distance from a current location to the destination;
provide guidance to reach the destination, wherein the output of the machine learning model provides the guidance through audio and visual indicators to a second individual in the emergency vehicle and wherein a light on a streetlight post flashes with a particular frequently along a route to the destination for the emergency vehicle to indicate the route to a driver of the emergency vehicle and to notify other vehicles of a location of the emergency vehicle on the route;
perform operations in a machine learning model, at the processing resource, the memory resource, or both, to determine and output a medical treatment procedure to provide to the individual by a another individual in the emergency vehicle that is responding to the individual based on the current state of the individual, the capability of the emergency vehicle that is responding to the individual to treat the individual, and the capability of the destination to treat the individual, and the distance from the initial location to the destination; and
provide audio and/or visual guidance to the another individual in the emergency vehicle for performing the medical treatment procedure on the individual, wherein the output of the machine learning model provides the guidance through audio and visual indicators to the another individual in the emergency vehicle.

8. The medium of claim 7, further comprising the instructions executable to provide guidance to follow the route to the initial location and provide guidance to reach the destination by showing the route to the initial location on a map and by showing a route to the destination on the map.

9. The medium of claim 7, further comprising the instructions executable to provide guidance to follow the route to the initial location and provide guidance to reach the destination by providing audible turn by turn instructions to the initial location and by providing audible turn by turn instructions to the destination.

10. The medium of claim 7, further comprising the instructions executable to provide guidance to reach the destination by instructing streetlights to flash along a route to the destination.

11. The medium of claim 7, further comprising indicating to other vehicles that an emergency vehicle is approaching by instructing streetlights to flash along a route to the destination.

12. A method, comprising:
receiving, at a processing resource, a memory resource, or both, location information of an individual and status information regarding a current state of the individual and a capability of an emergency vehicle that is responding to first individual;
performing operations in a machine learning model, at the processing resource, to determine and output a destination for the emergency vehicle that is responding to the individual, wherein the machine learning model determines the destination for the emergency vehicle based on the current state of the first individual, the capability of the emergency vehicle that is responding to the first individual to treat the first individual, a capability of the destination to treat the first individual, and a distance from a current location to the destination;
providing guidance to reach the destination based on the location information and the status information, wherein the output of the machine learning model provides the guidance through audio and visual indicators to a second individual in the emergency vehicle and wherein a light on a streetlight post flashes with a particular frequently along a route to the destination for the emergency vehicle to indicate the route to a driver of the emergency vehicle and to notify other vehicles of a location of the emergency vehicle on the route;
performing operations in a machine learning model, at the processing resource, to determine and output a medical treatment procedure to provide to the individual by another individual in the emergency vehicle that is responding to the first individual based on the current state of the individual, the capability of the emergency vehicle that is responding to the individual to treat the first individual, and the capability of the destination to treat the individual, and the distance from the current location to the destination; and
providing audio and/or visual guidance to the another individual in the emergency vehicle for performing the medical treatment procedure on the individual, wherein the output of the machine learning model provides the guidance through audio and visual indicators to the another individual in the emergency vehicle.

13. The method of claim 12, further comprising determining the destination based on traffic and/or road conditions.

14. The method of claim 12, further comprising determining the destination based on an amount of time needed to reach the destination.

15. The method of claim 12, further comprising determining, at the processing resource, a route to reach the individual based on the location information.

16. The method of claim 12, further comprising providing guidance to reach the destination via a route on a map and via audible turn by turn instructions.

17. The method of claim 12, further comprising providing guidance to reach the destination by providing instructions to cause streetlights to flash along a route to the destination.

* * * * *